United States Patent [19]
Govorchin

[11] Patent Number: 5,316,955
[45] Date of Patent: May 31, 1994

[54] FURNACE ATOMIZATION ELECTRON IONIZATION MASS SPECTROMETRY

[76] Inventor: Steven W. Govorchin, 360 Owl Dr., Louisville, Colo. 80027

[21] Appl. No.: 76,537

[22] Filed: Jun. 14, 1993

[51] Int. Cl.$^5$ ............................................. G01N 1/00
[52] U.S. Cl. ..................... 436/155; 422/78; 422/94; 436/174; 436/181; 436/153; 436/154; 250/288; 250/289
[58] Field of Search ............... 422/78, 94; 436/155, 436/85–86, 94, 173–174, 181, 153–154; 250/288–289

[56] References Cited

U.S. PATENT DOCUMENTS

| | | | |
|---|---|---|---|
| 3,619,839 | 11/1971 | Kraus et al. | 436/181 X |
| 4,278,441 | 7/1981 | Calcote et al. | 436/173 X |
| 4,673,656 | 6/1987 | Pink | 436/173 |
| 4,828,800 | 5/1989 | Castleman | 422/83 |
| 4,916,077 | 4/1990 | Forster et al. | 436/160 |
| 5,135,870 | 8/1992 | Williams et al. | 436/173 |

OTHER PUBLICATIONS

Bass & Holcombe, *Anal. Chem.*, 1987, 59:974–980.
Styris, *Fresenius Z. Anal. Chem.*, 1986, 323:710–715.
Styris, *Anal. Chem.*, 1984, 56:1070–1076.
Styris & Kaye, *Anal. Chem.*, 1982, 54:864–869.
Styris & Kaye, *Spectrochimica Acta*, 1981, 36B: 41–47.
Beauchemin, *Spectroscopy*, 7(7):12 (Sep. 1992).
Cantle (Ed.) & Robinson, "Atomic Absorption Spectrometry," New York, Elsevier, 1–5 & 22–23 (1982).
Cope, Kirkbright & Burr, *Analyst*, 107:611 (Jun. 1982).
Houk, *Analytical Chemistry*, 58(1): 97A (Jan. 1986).
Majer, "The Mass Spectrometer," London, Wykeham, 34–35 & 70–71 (1977).
Marcus, *Spectroscopy*, 7(5):12 (Jun. 1992).
Olesik, *Analytical Chemistry*, 63(1):12 A (Jan. 1991).
Perkin Elmer, Model 5100 PC and Zeeman/5100 PC Trade Literature (Oct. 1987).
Thermo Jarrell Ash, ICAP 61E Plasma Spectrometer Trade Literature (Apr. 1989).
Turner Scientific, TS SOLA Trade Literature (CA. 1990–1).
Varian, SpectrAA-300/400 Atomic Absorption Spectrometers Trade Literature (Feb. 1989).

*Primary Examiner*—Lyle A. Alexander
*Attorney, Agent, or Firm*—Christopher J. Rudy

[57] ABSTRACT

A resistively-heated furnace such as a graphite furnace is employed to atomize a sample for electron ionization and mass spectrometric analysis. Wide-ranging sample types such as biological tissue, semi-solid and nonhomogeneous materials, as well as bulk organic and inorganic chemicals, can be effectively and accurately analyzed with the instrument and instrumental method with little if any sample preparation.

18 Claims, 1 Drawing Sheet

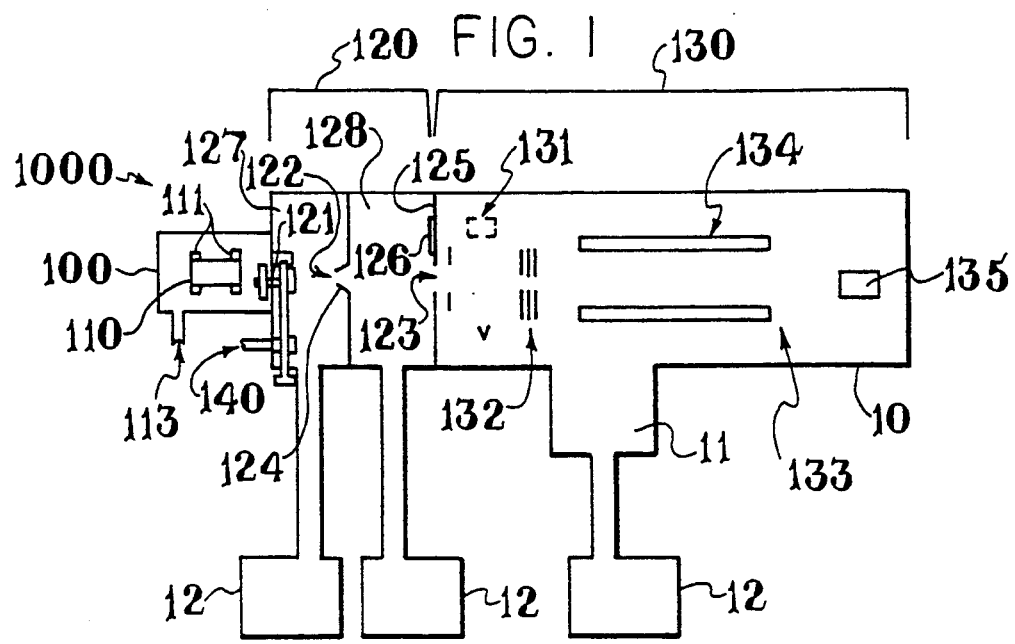
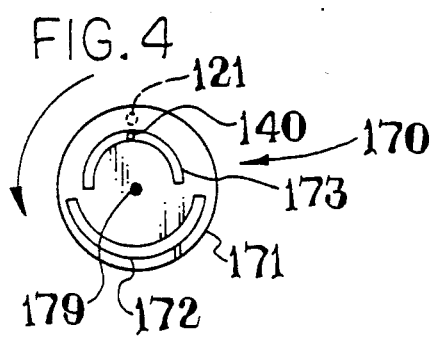
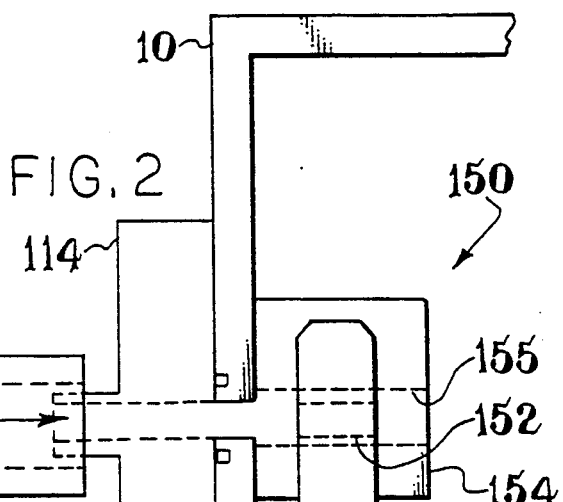
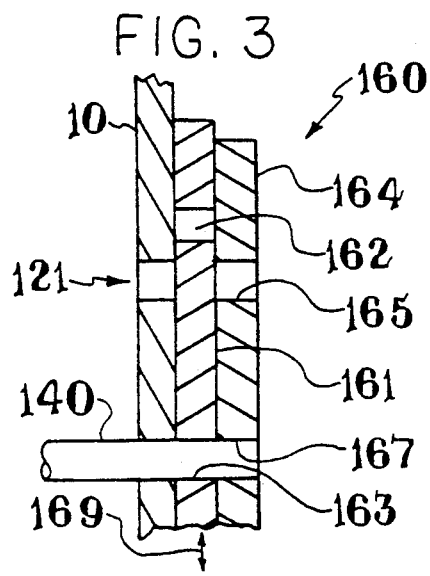

FURNACE ATOMIZATION ELECTRON IONIZATION MASS SPECTROMETRY

FIELD OF THE INVENTION

The present invention concerns a furnace atomization electron ionization mass spectral instrument and use thereof.

BACKGROUND TO THE INVENTION

Several types of instrumentation are presently available for elemental analyses. The four most predominant types are graphite furnace atomic absorbtion (GFAA), inductively coupled plasma optical emission spectrometry (ICP-OES), glow discharge mass spectrometry (GD-MS), and inductively coupled plasma mass spectrometry (ICP-MS). Each of these instruments with their associated techniques has its advantages and disadvantages in turn. There is no one form of instrumentation which is superior to the others in all respects.

GFAA is an optical technique. With it, an atom in its lowest energy state (the ground state) can absorb a specific wavelength of light which corresponds to the difference in the electronic energy levels of the excited and ground states of the atom. The more atoms of the particular analyte element which are present in a beam of this specific wavelength of light passing through the atoms, the greater will be the absorbance of that specific wavelength of light, and hence, the more absorbance will be measured. The amount of absorbance measured corresponds to the concentration of the analyte element in the sample. Principles of operation of atomic absorbtion have been described by J.W. Robinson in "Atomic Absorbtion Spectrometry," J.E. Cantle (Ed.), New York: Elsevier Scientific Publishing Co., pages 1-5 & 22-23, 1982. In GFAA, the sample is atomized in a resistively heated furnace. To absorb their characteristic wavelengths of light, analyte atoms must be free atoms, i.e., in the gas phase. See, M. Cope, G. Kirkbright & P. Burr, *Analyst,* 107, 611 (1982).

The main disadvantages of GFAA are its slow analysis rate, poor sensitivity with certain elements, and limited dynamic range. It is a slow technique because a different light source must be brought into use for every element to be analyzed. Its sensitivity varies according to how strongly a particular element absorbs light. For some elements, the absorbtion is very strong, but for others it is quite weak. For the weakly absorbing elements such as phosphorus and sulphur, the poor sensitivity results in very bad (high) detection limits. Its linear range of response is very dynamically limited. In general, its absorbance is directly proportional to analyte element concentration for solutions ranging from one part per billion (1 ppb) to 100 ppb. This represents two orders of magnitude. Above this range the absorbance begins to taper off and is no longer linearly related to concentration.

ICP-OES is also an optical technique. The ICP is a plasma which is maintained by the coupling of a radio frequency (RF) field with a stream of argon gas. It has been described by J. Olesik in *Anal. Chem.,* 63(1), 12A (1991). Its temperature of 6000 degrees Celsius or higher is hot enough to atomize almost any substance. It is also hot enough to excite ground state atoms to a higher energy level, from which emission of characteristic wavelengths of light can occur as the excited atoms settle back toward less energetic levels, again, the least energetic of which is the ground state. The intensities of these emissions are related to the concentration of analyte atoms in the sample. In ICP-OES, emissions are resolved and quantified by a spectrometer to include a detector such as a photomultiplier. See e.g., D. Beauchemin, *Spectroscopy,* 7(7), 12 (Sep. 1992).

ICP-OES has two main disadvantages associated with it relative to these other known techniques. It is subject to interferences because of the large number of emission lines inherent to atoms, which result in congested spectra. Also, it is not as sensitive as most of the other techniques.

GD-MS operates by ionizing the surface of a solid sample and analyzing the ions by mass spectrometry. A high voltage charges the sample in a low pressure argon plasma in order to accelerate argon ions toward the sample surface. The argon ions impact with the surface of the sample, dislodging free atoms, which become ionized as a result of further collisions in the plasma. In GD-MS, the plasma interfaces directly with the vacuum system that contains a quadrupole mass spectrometer. See e.g., R.K. Marcus, *Spectroscopy.* 7(5), 12 (Jun. 1992).

Disadvantages of GD-MS include that its sample must be electrically conductive, or made to be so, for it to be atomized. This is not always practical or even possible. At the very least, nonconductive samples such as biological samples and so forth must be mixed with a metal agent to make them conductive. This agent can be a source of contamination of the sample.

ICP-MS also generates ions from the sample and analyzes them by mass spectrometry. The atomization and ionization of the sample occurs in an inductively coupled plasma which is essentially the same as that in ICP-OES. The plasma is hot enough not only to atomize the sample but also to ionize most of the analyte atoms. In ICP-MS, however, the plasma generator is mounted so as to orient the plasma horizontally, and the plasma is directly interfaced to the inlet of a vacuum chamber for ion analysis. See, R. Houk, *Anal. Chem.,* 58, 97A (1986).

Disadvantages of ICP-MS include that interferences and a form of ion suppression are often unavoidable. This is caused by the atomization and ionization steps which occur in the same region, a wet argon plasma. The interferences result in relatively poor detection limits for important atoms such as Si, S, P, Cl, K, Ca, Sc, V, Mn, Cr, Fe and Se.

Another known mass spectrometric system employs a Knudson cell as its sample source. The cell is positioned internally, and is heated slowly under the vacuum of the instrument until its solid phase sample contents come into thermal equilibrium with its vapor phase and the cell. The vapors effuse through a small opening in the cell and travel to the ionization region as a molecular beam. The mass spectrometer measures the ion current resulting from the sample. The purpose of this instrument is to establish the vapor pressure of the atomic or molecular species inside the cell rather than to determine elemental analysis of a sample. See, J.R. Majer, "The Mass Spectrometer," London: Wykeham Publications, Ltd., Crane, Russak & Co., Inc., page 71, 1977.

Further art concerning such instruments, parts thereof, and so forth, and improvements in them is known. See e.g., Kraus et al., U.S. Pat. No. 3,619,839 (Nov. 16, 1971), for an electrically heatable cylindrical sample container; Calcote et al., U.S. Pat. No. 4,278,441

(Jul. 14, 1981), for a flame sampling apparatus and method; Pink, U.S. Pat. No. 4,673,656 (Jun. 16, 1987), for aerosol production in inductively coupled plasma emission spectroscopy; Castleman, U.S. Pat. No. 4,828,800 (May 9, 1989), for a system for trace gas detection; Forster et al., U.S. Pat. No. 4,916,077 (Apr. 10, 1990), for a method and apparatus for oxidative decomposition and analysis of a sample; Williams et al., U.S. Pat. No. 5,135,870 (Aug. 4, 1992), for laser ablation/ionization and mass spectrometric analysis of massive polymers. This is not a technique for elemental analysis. See also trade literature for the following instruments: Model 5100 PC and Seeman/5100 PC atomic absorbtion spectrometers (Perkin Elmer, 1987); SpectrAA-300/400 atomic absorbtion spectrometers (Varian, 1987); ICAP 61E plasma spectrometer (Thermo Jarrel Ash, 1989); TS SOLA modular mass spectrometer system for multi-element analysis of liquids and solids, ICP-MS & GD-MS in one instrument (Turner Scientific).

OBJECTS OF THE INVENTION

It is an object hereof to overcome disadvantage(s) of known instrumental analyses such as aforesaid. It is an object to provide a fundamentally novel instrument which can accommodate a wide range of samples and/or provide good detection capabilities.

Further objects hereof are extant.

SUMMARY OF THE INVENTION

The present invention provides a furnace atomization electron ionization mass spectrometric (FA-EI-MS) instrument, which comprises a vacuum housing, attachable external to the vacuum housing a resistively heatable sample atomization chamber where a sample can be introduced and at least a part of the sample can be atomized under a blanket of an inert gas, in communication with a first interior region of the vacuum housing where at least a part of a sample atomized in said chamber can be introduced, pass through, and be directed toward a second interior region of the vacuum housing, said first region being in communication with said second interior region where at least a part of the atomized sample can pass through and be influenced by an electron gun for ionizing at least a part of the atomized sample, and where at least a part of the ionized sample can further pass and be influenced and detected by a mass filter, said first and second regions being generally under vacuum, there being an inert gas inlet attachable onto openable into the vacuum housing for introduction of inert gas when atomized sample is not being introduced into said first region, and there being a control attachable to the vacuum housing for introduction of atomized sample into said first region. A method of use of the instrument to analyze a sample is also provided.

The invention is useful in elemental analysis.

The invention notably satisfies at least one if not all of its stated objects. Significantly, FA-EI-MS is well suited for use with many types of samples without much, if any, sample preparation. Biological tissues, semi-solid and nonhomogeneous materials as well as bulk organic and inorganic chemicals and mixtures can be the samples. It can perform semiquantitative, quantitative, and qualitative analyses on samples such as these without dissolution or other preparation. FA-EI-MS may have excellent sensitivity and linear dynamic range, and little or no appreciable fundamental interference and ion suppression.

Numerous further advantages attend the invention.

DRAWINGS IN BRIEF

The drawings form part of the specification hereof. In the drawings, like numerals refer to like features.

FIG. 1 is a schematic plan view of an FA-EI-MS, not to scale.

FIG. 2 is a cut-away side view of a control, or vacuum interface, twist type, of the FA-EI-MS of FIG. 1, not to scale.

FIG. 3 is a cut-away side view of another control, or vacuum interface, slide type, for an FA-EI-MS, not to scale.

FIG. 4 is a front schematic view of another control, or vacuum interface, rotating type, for an FA-EI-MS, not to scale.

ILLUSTRATIVE DETAIL

The purpose of the FA-EI-MS instrument is for qualitative and quantitative analyses of the elemental composition of a substance or sample. With reference to the drawings, principles of making and using the FA-EI-MS instrument are described.

Instrument 1000 has vacuum housing 10, preferably made in general of aluminum or stainless steel, which can have a vacuum generally maintained from turbo pump or diffusion pump 11 and mechanical pumps 12. Vacuum housing 10 may be of any suitable shape and dimension, preferably, say, about from 20 to 25 centimeters (cm) in general in diameter, and of suitable length or dimension to accommodate its internally spaced components. External to the vacuum housing is a resistively heatable sample atomization chamber 100 such as provided by a hollow graphite furnace 110 having electrical connections 111 where electricity is introduced to and passed through the graphite such that the resistance of the graphite to the electricity causes rapid heating of the furnace. The furnace has initial sample introduction orifice 112, which is preferably about from 1.8 to 2.0 millimeters (mm) in diameter, in communication with the interior of the furnace. Upon the heating, at least a part of the sample is atomized inside the furnace. The furnace is kept under a blanket of an inert gas such as argon (Ar) or helium (He) by inert gas inlet 113.

Sample atomization chamber 110 communicates with a first interior region 120, a two-stage vacuum interface zone, of the vacuum housing where at least a part of a sample atomized in the resistively heated sample atomization chamber can be introduced such as through atomized sample introduction orifice 121 leading to control valve 150, 160 or 170. First interior region 120 may be any suitable length, preferably, say, a length of about 15 cm to provide a path for the atomized sample to pass through. The introductory orifice 121 is suitably-sized, preferably about from 0.5 to 2.0 mm, e.g., approximately 1 mm, in diameter. Atomized sample passes through region 120 through columnator orifice 122, which is suitably-sized, preferably about from 0.7 to 1.0 mm in diameter, and columnator orifice 123, which is suitably-sized, preferably about from 1.0 to 2.0 mm in diameter. The mechanical pumps 12 draw vacuum, preferably to a pressure of about 10 millibar (mbar) in first stage 127 and of about 0.1 mbar in second stage 128 in the two-stage vacuum zone of the first interior region. The first interior orifice 122 may be on the tip of a skimmer cone 124, and the second interior orifice being on valve panel 125 which has a slide valve 126 to control introduction of material further into the instrument. The first interior region 120 communicates with a second interior region 130, the analyzer region, of the vacuum housing. Second interior region 130 may be any suitable length, preferably, say, a length of about 1 meter (m) to provide a path for the sample in its appropriate state to continue to pass through. In the second interior region, the atomized sample is influenced, as by an electron bombardment source or electron gun 131 for ionizing at least a part of the atomized sample. A Nier-type ion source may be employed as the electron gun. A common potential difference for use may be 70 volts (V), but dissociation patterns typically do not change greatly for voltages between 50 and 100 V. A voltage of 20 V may be employed, as may be the case with He carrier gas. See e.g., J.R. Majer, "The Mass Spectrometer," London: Wykeham Publications, Ltd., Crane, Russak & Co., Inc., pages 34–35, 1977. Ion optic unit 132 focuses the ionized sample. Also there, at least a part of the ionized sample can continue to pass and be influenced and detected by a mass filter system 133. The mass filter system can be such as quadrupole mass spectrometer 134, or alternatively a magnetic sector mass spectrometer, in effective arrangement with a suitable detector 135. Turbo pump 11 and mechanical pump 12 draw vacuum, preferably to a pressure of about 0.000001 mbar in the second interior region, and remove expended sample residue as gas and inert gas in the process.

With a quadrupole mass spectrometer and electron gun, atomized sample can be introduced for periods of time from about 0.5 to about 1.5 second in duration for measurement. Preferably, the sample is introduced for 1 second.

Alternatively, a time of flight mass spectrometer may be employed as a primary part of the mass filter system 131. In conjunction with this, a pulsed, or diverted electron stream, electron gun 127 is employed. In that case, diversions of the electron stream of less than 10 nanoseconds are possible. In correspondence, preferably the control valve 150 is in synchronization with such a system.

A housing inert gas inlet 140, which is preferably about from 1.5 to 3.2 mm in diameter, e.g., about from 1.588 to 3.175 mm in diameter, communicates a supply of inert gas into the vacuum housing when atomized sample is not being introduced into first region 120. The rate of inert gas supplied through this inlet is approximately that of atomized sample under inert gas blanket which enters through atomized sample introduction orifice 121. The control valve 150 or 160 may control flow of inert gas through the housing gas inlet as well.

The control valve, or vacuum interface, can be attached to the vacuum housing 10 for introduction of atomized sample into the first region 120. The control valve can be of the twist type 150. Alternatively, it might be of the slide type 160 or rotating type 170, among other types and modifications.

Twist type control valve 150 has rotary valve stem 151 such as made to include a polytetrafluoroethylene polymer such as a TEFLON polymer. The rotary valve stem has sample orifice 152, which is preferably about from 5 to 10 mm in diameter, and inert gas orifice 153, which is preferably about from 5 to 10 mm in diameter. The sample orifice and inert gas orifice are disposed such that their axes of flow are generally orthogonal to each other so that when one orifice permits flow, the other stops it, and vice versa. Upper valve assembly 154 such as made of stainless steel securely holds valve stem 151 tip therein and has orifice 155, which is preferably about from 14 to 15 mm in diameter. When atomized sample is to be introduced through atomized sample introduction orifice 121, orifices 121, 152 & 155 permit communication between sample atomization chamber 110 and first interior region 120. Lower valve assembly 156, also such as made of stainless steel, securely holds a lower portion of valve stem 151 therein and has orifice 157, which is preferably about from 14 to 15 mm in diameter. When pure inert gas is to be introduced through inert gas orifice 140, orifices 140, 153 & 157 permit communication between the pure inert gas supply and the housing interior. Support and sealing means 158 keep valve stem 151 in place and help retain vacuum. Handle 159 rotated in the direction of the proximate arrows can control inlet of atomized sample gas in its inert gas blanket, or inlet of pure inert gas. The valve stem may be mechanically operated. See, FIG. 2.

Slide type control valve 160 has base plate 161 such as made to include a polytetrafluoroethylene polymer such as a TEFLON polymer. The sliding valve base plate has sample orifice 162, which is preferably about from 5 to 10 mm in diameter, and inert gas orifice 163, which is preferably about from 5 to 10 mm in diameter. The sample orifice and inert gas orifice are disposed apart such that when one orifice is in registry with corresponding orifices to include in housing 10 the other is out of registry with its correspondent orifices. As well, the latter correspondent orifices are closed off by the solid base plate 161. Sliding valve backing assembly 164 holds base plate 161 firmly in place and seals it so that there may be little, if any, leakage during operation. Sliding valve backing assembly 164 has orifice 165, which is preferably about from 5 to 10 mm in diameter. When atomized sample is to be introduced through atomized sample introduction orifice 121, orifices 121, 162 & 165 permit communication between sample atomization chamber 110 and first interior region 120. Sliding valve backing assembly 164 securely holds a lower portion of the sliding valve base plate 161 therein and has orifice 167, which is preferably about from 5 to 10 mm in diameter. When pure inert gas is to be introduced through inert gas orifice 140, orifices 140, 163 & 167 permit communication between the pure inert gas supply and the housing interior. Arrow 169 indicates the direction which the base plate 161 may be oscillated. The valve base may be mechanically operated. See, FIG. 3

Rotating disc valve 170, akin to the slide type valve 160, may be employed. There, suitably balanced wheel 171 has sample introducing orifice 172 and inert gas introducing orifice 173. One orifice is suitably further from axle 179 than the other, and they are opposed, such that when the wheel rotates about the axle, one is in registry with its corresponding or correspondent housing orifices when the other is not. Preferably, each of these orifices is about from 5 to 10 mm in width. The wheel may be, and preferably is, mechanically operated. See, FIG. 4.

Thus, in general, the FA-EI-MS instrument embraces three main component groups:

1) A means for sample atomization, e.g., a graphite furnace, with vacuum interface accessory.
2) A means for ionization, i.e., a suitable electron gun.
3) A means for mass filtering, i.e., the mass spectrometer, e.g., a quadrupole or magnetic sector mass spectrometer with an electron multiplier-type detector, or a time of flight mass spectrometer with a dual microchannel plate detector.

The three main component groups are generally discussed in turn.

In typical atomization, the sample to be analyzed (the analyte) is placed in the resistive heating furnace, e.g., the graphite furnace, while the furnace is at room temperature. Then the furnace is resistively heated under inert atmosphere. For example, a graphite furnace generally can be heated to any desired temperature up to 3000 degrees Celsius by varying the current passing through it. Heating the furnace to intermediate temperatures is done to boil off any solvent and also to ash the sample. The ashing step is done to render certain volatile analyte elements less volatile so that they do not sublime away or boil off prematurely. The furnace is ultimately heated to temperatures approaching the maximum to bring about atomization of the sample. This type of atomization is commonly known as electrothermal atomization. See e.g., J.W. Robinson in "Atomic Absorbtion Spectrometry," J.E. Cantle (Ed.), New York: Elsevier Scientific Publishing Co., pages 22-23, 1982.

When the desired temperature has been reached and the sample has been vaporized and atomized, contents of the furnace are permitted to pass into the two-stage vacuum interface region of the instrument by means of a suitable sample valve. The trajectories of the sample atoms carry them through this first region and into the analyzer region, which is the second internal region of the instrument. When the sample valve closes off passage of atomized sample, a constant pure inert gas flow is admitted into the housing, preferably about the vacuum interface region. When the sample valve is opened, the inert gas flow is cut off by corresponding valve action. This opposing flow of sample or pure inert gas minimizes the pressure change in the system when contents of the furnace are introduced.

The analyzer chamber contains the electron gun and mass spectrometer. Upon entering this chamber a fraction of the neutral atoms is ionized by collisions with a beam of electrons from the electron gun. The neutral atoms become positively charged ions as a result of the loss of electrons due to impacts with the electron beam. The ions are then accelerated towards the inlet of the mass spectrometer by means of an electric potential. See e.g., J.R. Majer, "The Mass Spectrometer," London: Wykeham Publications Ltd., Crane, Russak & Co., Inc., pages 34-35, 1977.

The mass filter may be a quadrupole mass spectrometer, which is basically a set of four rods to which RF and DC voltages are applied in such a way that ions will be deflected off course and not pass through unless they have the mass-to-charge ratio which has been selected at that moment. The RF and DC voltages can be rapidly changed to permit ions of any desired mass-to-charge ratio pass through. Application of the quadrupole mass spectrometer to elemental analysis has been described by R. Houk, *Anal. Chem.*, 58, 97a (1986). Other kinds of mass spectrometers can be substituted here although the quadrupole is the best suited low resolution device for this application. However, in the case of the time of flight mass spectrometer, increased ion transmission results in greater sensitivity. Nevertheless, the time of flight mass spectrometer is best suited with pulsed sample sources.

The ions which complete their journey through the quadrupole impact on the detector. The impacts are converted to current signals which are then registered by data acquisition equipment. However, in the case of the time of flight mass spectrometer, it is the absolute flight time from the ionization site to the detector which is measured and used to determine masses.

Computer processing of the data is desirable.

The major components for atomization, ionization and mass resolution are available commercially or otherwise may be made or adapted. Similarly, computer processing equipment and software are available commercially or otherwise may be made or adapted.

The FA-EI-MS has certain advantages over known techniques.

For instance, in comparison with GFAA, FA-EI-MS can rapidly scan over the entire mass range, from the lightest to the heaviest isotopes, with each sampling, and thus, it is much faster than GFAA. It will perform much better on the weakly absorbing elements such as P and S. The electrons which the FA-EI-MS uses to ionize the neutral atoms will have more than sufficient energy to ionize every atomized element. Since ionization energy is not a problem, FA-EI-MS sensitivity will be high for elements across the entire mass range. The FA-EI-MS may have up to approximately six orders of magnitude of linear dynamic range as is characteristic of, for example, similar quadrupole mass spectrometers. Analogously good results may be obtained with the time of flight mass spectrometer. This is a great advantage because little sample preparation or dilution is necessary to have the analyte element concentration fall within workable range for accurate FA-EI-MS quantitative determination.

In comparison with ICP-OES, the FA-EI-MS spectra appear uncongested. This is because, in FA-EI-MS spectra, the number of lines is limited to the number of isotopes which naturally occur. Moreover, the detection limits of which FA-EI-MS is capable are about 10 to 100 times better than ICP-OES.

Although GD-MS and ICP-MS are techniques similar to FA-EI-MS in terms of the mass spectrometric equipment, these techniques significantly differ in the ways in which they atomize the sample and form ions from the atoms. Accordingly, accuracy, precision and detection limits vary significantly.

In comparison with GD-MS, the sample to be tested in FA-EI-MS does not have to be electrically conductive to be atomized. The resistively heatable, e.g., graphite, furnace of FA-EI-MS can heat everything that is inside it regardless of whether it is conductive or not. Therefore, FA-EI-MS offers less potential for adulteration or contamination of nonconductive samples than GD-MS, and accordingly, its more accurately determinable sample range is much wider.

In comparison with ICP-MS, the sample to be tested in FA-EI-MS can be made to be dry during the atomization step, and if necessary, He can be substituted for Ar as the inert blanket or sheath gas around the furnace. This removes the fundamental causes which give rise to the interferences which trouble ICP-MS. Thus, it has good detection limits for important atoms, not only P and S, but also for such atoms as Si, Cl, K, Ca, Sc, V, Mn, Cr, Fe and Se. Also, since the FA-EI-MS atomizes and ionizes in two physically separate regions, the suppression effect observed in ICP-MS generally does not arise in FA-EI-MS.

In comparison with the internally positioned Knudsen cell sample source device, the FA-EI-MS has its atomization furnace positioned externally, and it is heated and analyses are taken much more rapidly. The FA-EI-MS can accommodate a much wider range of sample capability, not being restricted to solid-phase Knudson cells. Moreover, the FA-EI-MS determines, not atomic or molecular vapor pressures, but true elemental analysis.

In general, the FA-EI-MS is highly versatile and accurate. It is suitable for analyzing a wide variety of sample matrices. A general requirement is that the sample boiling point must not be above the temperature of the resistively heatable furnace, e.g., 3000 degrees Celsius with a carbon furnace, and only a few elements have boiling points which are higher than this.

CONCLUSION

The present invention is thus provided. Numerous adaptations can be effected within its spirit, the asserted scope of which is particularly pointed out as follows:

I claim:

1. A furnace atomization electron ionization mass spectra (FA-EI-MS) instrument, which comprises a vacuum housing, attachable external to the vacuum housing a resistively heatable sample atomization chamber where a sample can be introduced and at least a part of the sample can be atomized under a blanket of an inert gas, in communication with a first interior region of the vacuum housing where at least a part of a sample atomized in said chamber can be introduced, pass through, and be directed toward a second interior region of the vacuum housing, said first region being in communication with said second interior region where at least a part of the atomized sample can pass through and be influenced by collision with a beam of electrons from an electron gun in said second region for ionizing at least a part of the atomized sample, and where at least a part of the ionized sample can further pass, be accelerated towards by means of an electric potential, and optionally be influenced by a magnetic field of and be detected by a mass filter, said first and second regions being generally under vacuum, there being an inert gas inlet attachable onto openable into the vacuum housing for introduction of inert gas when atomized sample is not being introduced into said first region, and there being a control attachable to the vacuum housing for introduction of atomized sample into said first region, such that when atomized sample is not being introduced into the vacuum housing inert gas is introduced through the inert gas inlet and when atomized sample is being introduced into a vacuum housing inert gas glow is cut off so as to create opposing flows of sample and inert gas so as to minimize pressure change in the instrument when contents of the furnace are introduced therein.

2. The FA-EI-MS instrument of claim 1, wherein the control includes a slide-type valve.

3. The FA-EI-MS instrument of claim 1, wherein a computer is in communication with at least the detector of the instrument for processing of accumulated data.

4. The FA-EI-MS instrument of claim 1, wherein the mass filter includes a quadrupole mass spectrometer and a suitable detector.

5. The FA-EI-MS instrument of claim 4, wherein the control includes a twist-type valve.

6. The FA-EI-MS instrument of claim 1, wherein the electron gun is a pulsed electron gun, and the mass filter includes a time of flight mass spectrometer and a suitable detector.

7. The FA-EI-MS instrument of claim 6, wherein the control includes a rotary-type valve.

8. The FA-EI-MS instrument of claim 1, wherein the resistively heated atomization chamber is a graphite furnace.

9. The FA-EI-MS instrument of claim 8, wherein the inert gas provided is argon.

10. The FA-EI-MS instrument of claim 8, wherein the inert gas provided is helium.

11. The FA-EI-MS instrument of claim 8, wherein the mass filter includes a quadrupole mass spectrometer and suitable detector.

12. The FA-EI-MS instrument of claim 11, wherein the control includes a twist-type valve.

13. The FA-EI-MS instrument of claim 8, wherein the electron gun is a pulsed electron gun, and the mass filter includes a time of flight mass spectrometer and a suitable detector.

14. The FA-EI-MS instrument of claim 13, wherein the control includes a rotary-type valve.

15. A method of elemental analysis comprising steps of (A) providing a furnace atomization electron ionization mass spectra (FA-EI-MS) instrument, which contains a vacuum housing, attachable external to the vacuum housing a resistively heatable sample atomization chamber where a sample can be introduced and at least a part of the sample can be atomized under a blanket of an inert gas, in communication with a first interior region of the vacuum housing where at least a part of a sample atomized in said chamber can be introduced, pass through, and be directed toward a second interior region of the vacuum housing, said first region being in communication with said second interior region where at least a part of the atomized sample can pass through and be influenced by collision with a beam of electrons from an electron gun in said second region for ionizing at least a part of the atomized sample, and where at least a part of the ionized sample can further pass, be accelerated towards by means of an electric potential, and optionally be influenced by a magnetic field of and be detected by a mass filter, said first and second regions being generally under vacuum, there being an inert gas inlet attachable onto openable into the vacuum housing for introduction of inert gas when atomized sample is not being introduced into said first region, and there being a control attachable to the vacuum housing for introduction of atomized sample into said first region, such that when atomized sample is not being introduced into the vacuum housing inert gas is introduced through the inert gas inlet and when atomized sample is being introduced into the vacuum housing inert gas flow is cut off so as to create opposing flows of sample and inert gas so as to minimize pressure change in the FA-EI-MS instrument when contents of the furnace are introduced therein;

(B) providing a sample and introducing it into the resistively heatable sample atomization chamber at a temperature about or below room temperature;

(C) rapidly heating the resistively heatable sample atomization chamber to a suitable temperature, which can include to a temperature of up to about 3000 degrees Celsius, under an inert gas blanket such that at least a part of the sample becomes atomized, while introducing a small stream of pure inert gas through the inert gas inlet into the FA-EI-MS instrument;

(D) introducing atomized sample into said first region of the FA-EI-MS instrument such that it passes therethrough and into said second region where at least a part of it is ionized by the electron gun, in said second region accelerated towards by means of the electric potential and influenced by the mass filter, and detected, while stopping the small stream of pure inert gas from entering into the FA-EI-MS instrument, and (E) analyzing the results.

16. The method of claim 15, where the sample is a non-electrically conductive biological sample.

17. The method of claim 15, where the inert gas is helium.

18. A furnace atomization electron ionization mass spectra instrument, comprising a vacuum housing, attachable external to the vacuum housing a resistively heatable sample atomization chamber where a sample can be introduced and at least a part of the sample can be atomized under a blanket of an inert gas, in communication with a first interior region of the vacuum housing where at least a part of a sample atomized in said chamber can be introduced, pass through, and be directed toward a second interior region of the vacuum housing, said first region being in communication with said second interior region where at least a part of the atomized sample can pass through and be influenced by collision with a beam of electrons from an electron gun in said second region for ionizing at least a part of the atomized sample, and where at least a part of the ionized sample can further pass, be accelerated towards by means of an electric potential, and optionally be influenced by a magnetic field of and be detected by a mass filter, said first and second regions being generally under vacuum, there being an inert gas inlet attachable onto openable into the vacuum housing for introduction of inert gas when atomized sample is not being introduced into said first region, and there being a control attachable to the vacuum housing for introduction of atomized sample into said first region, such that when atomized sample is not being introduced into the vacuum housing inert gas is introduced through the inert gas inlet and when atomized sample is being introduced into the vacuum housing inert gas flow is cut off so as to create opposing flows of sample and inert gas so as to minimize pressure change in the instrument when contents of the furnace are introduced therein, said instrument being constructed to solely provide mass spectral analysis of the sample.

* * * * *